United States Patent [19]
Antoshkiw et al.

[11] Patent Number: 4,471,779
[45] Date of Patent: Sep. 18, 1984

[54] MINIATURE BALLOON CATHETER

[75] Inventors: William T. Antoshkiw, Clifton; Thomas A. Ursic, Princeton, both of N.J.

[73] Assignee: Becton, Dickinson and Company, Paramus, N.J.

[21] Appl. No.: 717,746

[22] Filed: Aug. 25, 1976

[51] Int. Cl.³ .................. A61M 25/00; A61B 17/12
[52] U.S. Cl. ................................. 128/325; 128/344
[58] Field of Search ............... 128/325, 348, 349 B, 128/349 BV, 246, 344

[56] References Cited

U.S. PATENT DOCUMENTS

| 3,795,246 | 3/1974 | Sturgeon | 128/325 |
| 3,834,394 | 9/1974 | Hunter | 128/325 |
| 4,029,104 | 6/1977 | Kerber | 128/325 |
| 4,085,757 | 4/1978 | Pevsner | 128/325 |

OTHER PUBLICATIONS

Dow Corning Bulletin, vol. 2, No. 3 Jul. 1960 (p.9).

Primary Examiner—Dalton L. Truluck
Attorney, Agent, or Firm—Charles R. Hoffmann

[57] ABSTRACT

Improved detachment and sealing mechanism for a balloon catheter assembly utilized in diagnostic and therapeutic environments in connection with very small human vessels. The assembly is of the type including a resilient elongated catheter having means at one end for attachment to a source of pressurized fluid. A small inflatable tubular balloon is detachably connected at the other end of the cannula and is in fluid communication therewith. The detachment and sealing mechanism includes a self-sealing plug positioned in the balloon adjacent the end of the cannula. A circumferential band is on the outer surface of the inflatable balloon in concentric position with respect to the plug. A pin is provided and has a passageway therethrough and one end mounted in the end of the cannula with the passageway therein in communication with the passageway through the cannula and the other end of the pin being pointed and extended through a small opening in the plug in fluid communication with the balloon on the side of the plug distal from the cannula. The pin extending through the plug expands the plug and the expandable band surrounding the plug. The pin has a side opening intermediate its ends located in the space between the end of the cannula and the adjacent end of the plug. When sufficient pressurized fluid is passed through the cannula and the pin into the inflatable portion to inflate the balloon to the desired degree, further fluid passes through the side opening in the pin and inflates the end portion surrounding the plug and extending to the end in communication with the cannula thereby freeing the cannula and pin from the balloon portion for removal. Thereafter, the band and self-sealing plug will cooperate to return to their initial configuration and close the opening in the plug and retain the balloon in inflated condition in position in the human vessel.

7 Claims, 9 Drawing Figures

MINIATURE BALLOON CATHETER

BACKGROUND OF THE INVENTION

Catheterization and in particular the use of a balloon type catheter has been known to the medical profession for many years. The general environment of use for these catheters has been for entering large body cavities or for use in connection with large body passageways. Until recently it has not been considered or even deemed feasible for use of a balloon type expanding device within small body vessels where delicate and precision techniques are employed.

Significant advancement in this area has been recently deemed to be feasible. The theory is that a balloon catheter technique is possible for catheterization of human cerebral blood vessels. With this technique it is possible to investigate collateral blood flow, intraarterial pressure, brain temperature, the vital staining of tumors, and the introduction of chemical agents. Temporary occlusion of the internal carotid artery makes possible angiography of the external carotid, while occlusion of separate branches of the external carotid permits selected angiography of its functioning branches. Also, considered is the use of a balloon catheter in investigating arteriovenous and carotid-cavernous fistulas. It is now deemed possible to occlude the cavity of arterial aneurysms or the afferent vessels of arteriovenous aneurysms. Furthermore, it is also believed useful as a means to shut off the blood flow to arterial aneurysms and carotid-cavernous fistulas when access is difficult. Also contemplated is the reconstruction of the cavernous part of the carotid artery in cases of carotid-cavernous fistulas.

It is considered that a general theory breakthrough has been made in the use of balloon catheters and it is a matter of development of catheter devices and techniques which will bring the theories into fruition.

SUMMARY OF THE INVENTION

With the above background in mind, it is among the primary objectives of the present invention to provide a device which will accomplish the theories of use and balloon catheterication as set forth above. The device is designed for use with selected arteries. The application is to cerebral angiography diagnosis and therapy including the following procedures; selective catheterization of tumor arterial supply e.g. distal anterior, post or middle cerebral artery with or without theraputic infusion, occlusion of vessel by the release of a dilated balloon as applied to arteriovenous malformation and carotid cavernous fistula. The device is also adaptable for visceral angiography including the super-selective catheterization for tumor evaluation and theraputic arterial occlusion for gastrointestinal hemmorrhage. A further application which is envisioned deals with super selective caronary angiography.

The balloon device is a flow directed three stage pressure controlled device used for either super-selective angiography perfusion and/or as a permanently implanted occlusion and/or reservoir device. In general, the device consists of a diagnostic and/or theraputic balloon mounted on the distal end of a section of plastic tubing in the form of a cannula.

The balloon device is adapted to be introduced into the bloodstream through a larger catheter previously inserted into the vessel. The device is then partially inflated and is propelled by the flow of the bloodstream to the identified area of investigation. This area could be, for example, an aneurysms, arteriosclerotc blockage, cancerous growth, anatomic anomaly, etc. Once in the desired location, pressure is used to inflate the balloon to totally occlude the blood vessel. Further pressure is then used to effect the function of the device such as perfusion and/or permanent occlusion.

The various types of devices employed in carrying out the invention are basically of three functional types. The first is for perfusion, the second is for implant and the third is a device for combined perfusion and implant.

In the perfusion type of device the balloon initially is in the uninflated state, usually filled with a radiopaque dye. The balloon is then partially inflated and is propelled by the bloodstream to the desired location. The device is then inflated to occlude the blood vessel. Further pressure is then applied and a valve type opening in the distal portion of the balloon opens at this increased pressure and a constant stream of radiopaque media is injected. In this situation, the balloon has blocked the upstream blood flow and the dye is therefore not washed out as occured during standard radiographic procedures. The downstream portion of the vessel is thereby fully filled with radiopaque dye. The device is flow directed and is pressure controlled in three stages.

The implant type of device includes a balloon initially in the uninflated state, usually filled with a radiopaque dye. The balloon is then partially inflated and is propelled by the bloodstream to the desired location. The device is then inflated to occlude the blood vessel. Further pressure is then applied which effects the permanent attachment of the balloon which remains filled with radiopaque dye for an extended period of time.

The devices includes a detachable holding mechanism and a self-sealing mechanism. The self-sealing ability is effected by means of a small portion of elastomeric material through which a pin hole has been placed by means of a wire. In the miniturized sizes that have been developed, an exteriorly mounted compression ring or rings are used to seal the proximally located portion of the balloon. A communicating cannula or hollow pin allows the device to be inflated or deflated prior to detachment. The detachment ability is effected by the communicating cannula or hollow pin. The cannula or pin communicating through the valve structure in the body of the balloon prior to detachment, has a side hole communicating into a chamber formed distally by the valve structure and proximally by the proximal portion of the device that has been stretched over the cannula. Pressurized fluid is an effective mechanism for detaching the stretched portion of the balloon device from the attached cannula. Pressure is communicated into the chamber through the side hole and detachment is effected. The inner pin does not hold the balloon device onto the catheter and, therefore, easily slides out of the self-sealing valve. The compression rings effect the total seal of the valve along with the self-sealing plug of elestomeric material.

The combination perfusion and sealing device combines the features of both of the above types of devices into one balloon that, after detachment, would continue to proximally perfuse dyes or drugs distal to the location of the balloon.

In summary, in general, the present device deals with a miniturized balloon catheter assembly adapted for use in diagnosis and therapy procedures in connection with small human vessels. The device includes a resilient catheter having means at one end for attachment to a source of pressurized fluid and having a small outer diameter for insertion into small human vessels. An inflatable tubular balloon is mounted on the other end of the cannula and is in fluid communication therewith. The cannula and balloon are adapted to be carried by the fluid in the vessel to a desired location therein. The source of pressure is utilized to inflate the balloon and to effect perfusion and detachment as desired. The detachment is accomplished through the use of self-sealing elestomatic plug mounted in the end portion of the balloon and spaced from the end of the cannula and at least one compression ring surrounding the exterior of the balloon in concentric position with respect to the plug. A hollow pin is mounted with one end extending through the plug and the other end in fluid communication and mounted on the cannula. The pin has a side opening to permit fluid to pass therefrom and expand the end portion of the balloon sufficiently to permit detachment of the cannula and pin from the balloon whereupon the compression ring and self-sealing plug will seal the end of the balloon from which the pin has been removed.

With the above objectives among others in mind, reference is had to the attached drawings.

DESCRIPTION OF THE PREFERRED EMBODIMENT

Figure 1:
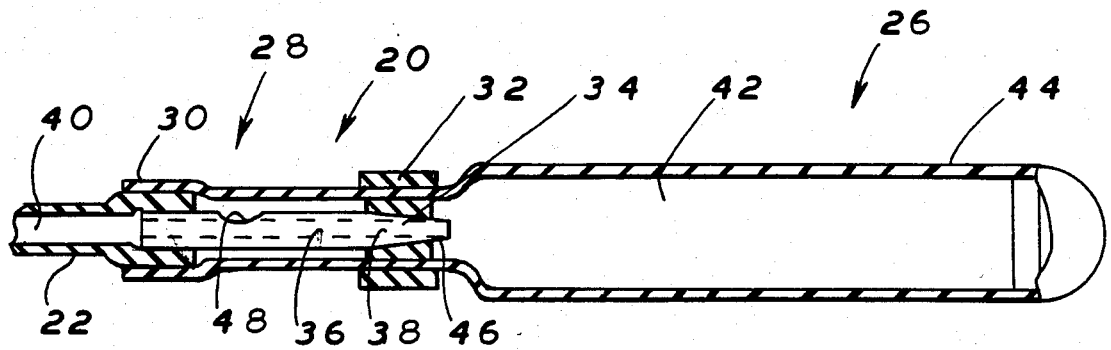
FIG. 1 is a fragmentary partial sectional view of the balloon catheter assembly of the invention.

FIG. 1 shows the catheter assembly 20 which includes a hollow cannula 22, open at both ends, with a connector 24 at one end which is adapted for connection to a conventional source of pressurized fluid. Mounted on the other open end of cannula 22 is an inflatable balloon portion 26. The proximal end portion 28 of the balloon terminates in an end 30 which is expanded to cover and frictionally engage the adjacent end of cannula 22. Spaced from end 30 on portion 28 is an expandable ring 32 which is concentrically aligned with an inner plug 34. The plug is of an expandable elastomeric self-sealing material and is provided with a small pin hole which may be formed by a wire. Ring 32 and plug 34 are both elastomeric materials and tend to compress when relaxed to form a seal at the proximal end portion 28 of the balloon as will be discussed in detail below.

A hollow pin 36 is located within inflatable balloon portion 28. Pin 36 has a through passageway 38 which communicates at one end with the through passageway 40 of cannula 22 and at the other end communicates with the chamber 42 in the main body portion 44 of balloon 26.

The communication between the pin and cannula 22 is accomplished by expanding cannula 22 over the adjacent end of the pin. The communication at the other end of the pin is accomplished by passing the pointed elongated beveled tip 46 through plug 34 so that the open end of the tip is in communication with chamber 42. In this manner there is through communication from cannula 22 to the chamber 42 in balloon 26. Additionally the cannula is interconnected with the balloon by means of attachment between the outer surface of the cannula and end portion 30 of the balloon and the inner surface of the cannula and the adjacent end 36. The other end of the pin is mounted in elastomeric plug 34 which frictionally engages the pin so as to assist in holding the assembly together until detachment is desired.

Pin 36 also includes a side opening 48 located between plug 34 and the end of cannula 22. This side opening 48 is utilized for activating the detachment between inflatable balloon 26 and cannula 22.

Figure 7:
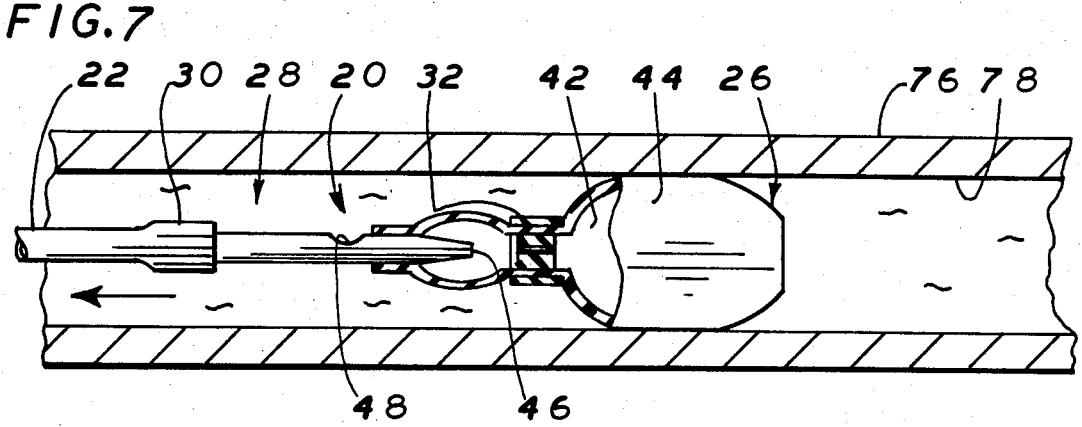
FIG. 7 is a fragmentary sectional view thereof showing the direction of removal of the cannula and pin from the remainder of the assembly subsequent to introduction of additional fluid after the balloon has been fully inflated and is sealed against the walls of the vessels.
Figure 8:
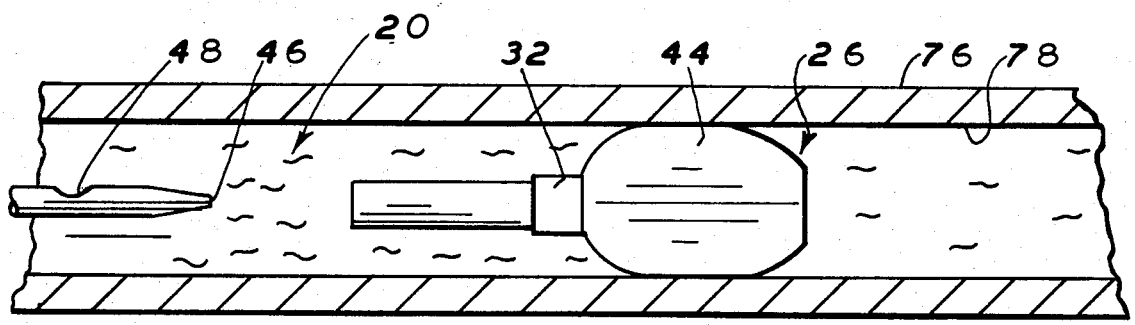
FIG. 8 is a fragmentary sectional view thereof showing the pin and cannula fully removed from the remainder of the assembly and the sealing means sealing the inflated balloon to retain it in fixed position against the walls of the vessel.
Figure 9:
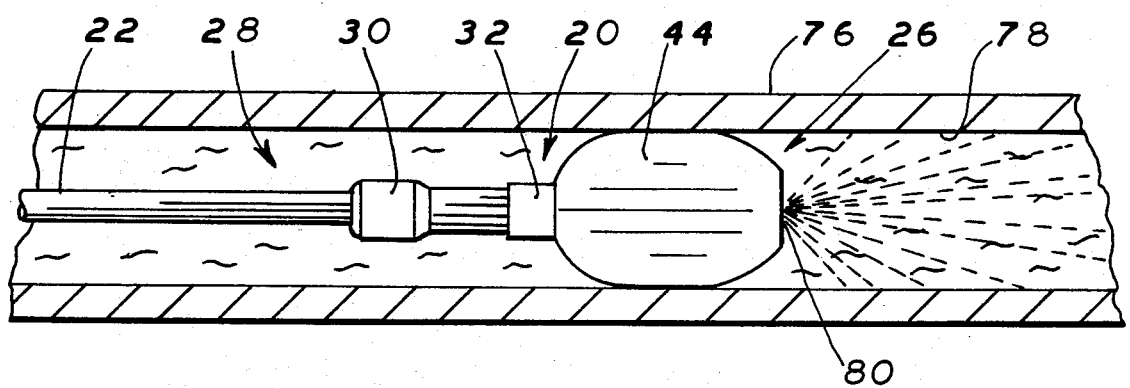
FIG. 9 is a fragmentary sectional view of the assembly with additional pressure being introduced to open the aperture in the distal end of the balloon so that the device acts as a perfusion device.

Operation and use of the embodiment of FIG. 1 is shown in sequential steps in FIGS. 4-8 of the drawings. The use of the device 20 as a perfusion device is depicted in FIG. 9 of the drawings.

Materials which can be used for the components of catheter assembly 20 include the following. For cannula 22, a plastic such as polyethylene or any conventional substitute therefor and for the expandable balloon portion 26, silastic tubing or any conventional substitute therefor which is elastomeric in nature so that it is inflatable in contrast to the cannula 22 under the same pressure condition has been found to be acceptable. It should be noted that the greater elasticity of inflatable portion 26 permits its manual expansion over the end of cannula 22 to facilitate interconnection therebetween. Pin 36 can be of any conventional semi-rigid or rigid metal or plastic materials such as stainless steel and plug 34 and compression ring 32 is formed of a conventional elastomeric self-sealing material such natural or synthetic rubber or any other conventional well known substitute therefor.

Figure 2:
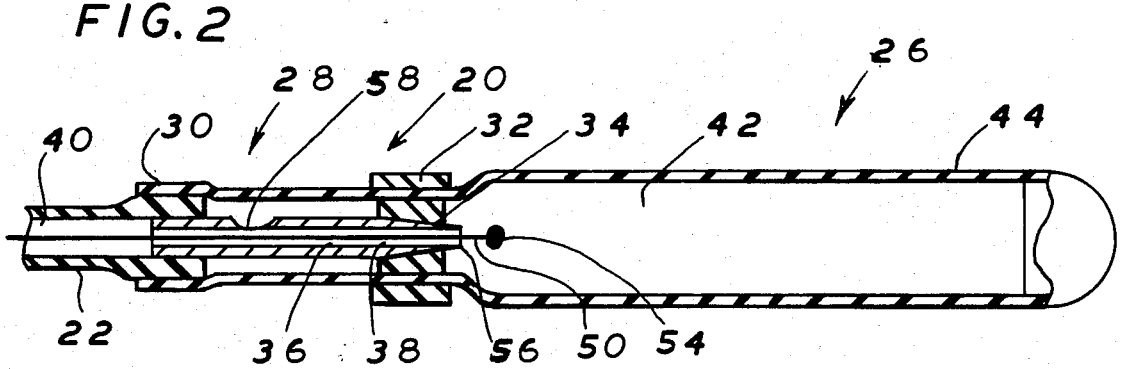
FIG. 2 is a fragmentary partial sectional view of an alternative balloon catheter assembly of the invention.

FIG. 2 of the drawings is the same as the FIG. 1 embodiment with the exception of an additional wire 50 which passes through the through passageway in the device 52 and terminates in a stop at the end of the wire in the form of a sphere 54. Naturally other configurations for the stop can be readily contemplated. The wire is of smaller diameter than the passageway so that fluid can by-pass the wire and inflation can occur to the desired degree. Then the wire can be withdrawn to block the open end of tip 56 by engagement with stop 54 which closes the opening. Thereafter, further pressure will only be able to exit through side opening 58 to accomplish detachment. In this manner, no further expansion of the balloon occurs during the detachment proceeding. All fluid passes through the side opening.

Figure 3:
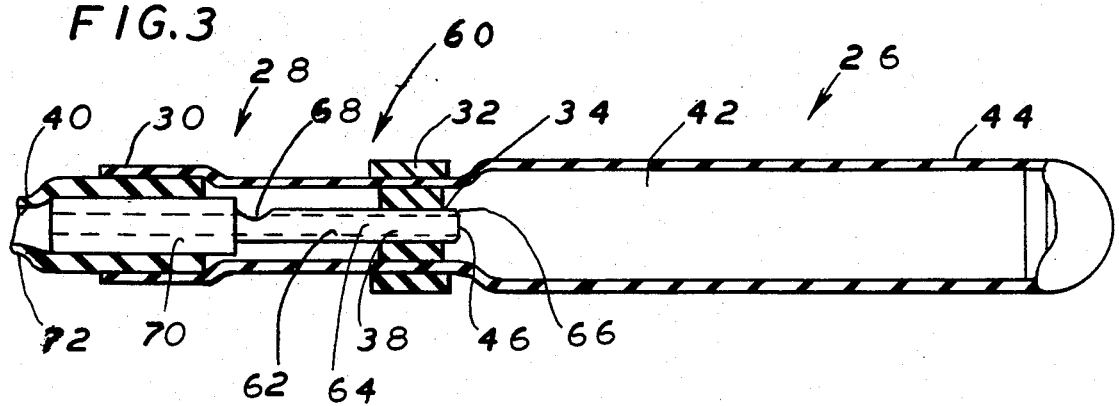
FIG. 3 is a fragmentary partial sectional view of a second alternative balloon catheter assembly of the invention.

The device 60 depicted in FIG. 3 is an alternative form which is identical to the previously discussed two embodiments with the exception of the configuration of the inner pin 62. Instead of the elongated beveled tip of the previous forms, the end portion 64 is of substantially the same outer diameter throughout its entire length with the exception of a small beveled edge 66 at the tip. The side opening 68 is approximately in the same location intermediate the ends of the pin, however, the proximal portion 70 of the pin is of a larger outer diameter than the portion of the pin from the side opening to the distal end. This larger diameter portion 70 facilitates further expansion of the end of cannula 72 and, accordingly, results in a tighter frictional interengagement therebetween so as to facilitate detachment of the cannula and pin together from the remainder of the assembly during the detachment operation. In all other respects the present structure operates the same as in the previous embodiments and accordingly, a discussion of the operation of the embodiment of FIG. 1 in the manner described below will reflect similar operation of the embodiments of FIGS. 2 and 3.

Naturally the dimensions of catheter assembly 20 is a matter of choice depending upon the particular human vessel to which it is to be applied, keeping in mind, that the device is to be used in very small human vessels. In any event, the length and lateral dimensions are determined by use. Furthermore, in addition to expanding the balloon portion to engage the outer surface of the cannula, it is also possible to shrink the end of the balloon portion on the end of the cannula to produce the same result.

A common technique for inserting the device 20 is to first introduce into vessel 76 a catheter of larger diameter and then passing catheter assembly 20 through the catheter of larger diameter and into the vessel. The outer catheter can then be removed or retained in position during the remainder of the operable procedures. The larger catheter can be used with all of the previously discussed embodiments.

Figure 4:
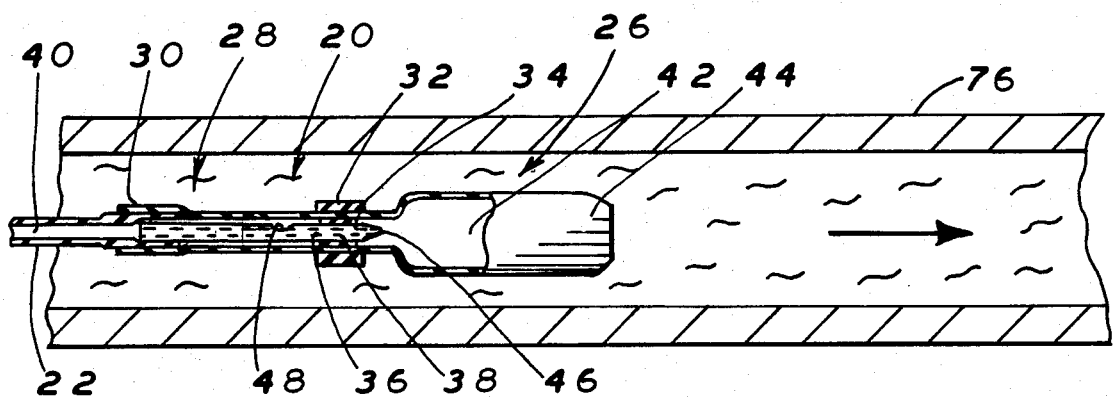
FIG. 4 is a fragmentary sectional view of the assembly of FIG. 1 inserted in a small human vessel prior to inflation thereof with an arrow showing the direction of flow of blood in the vessel.
Figure 5:
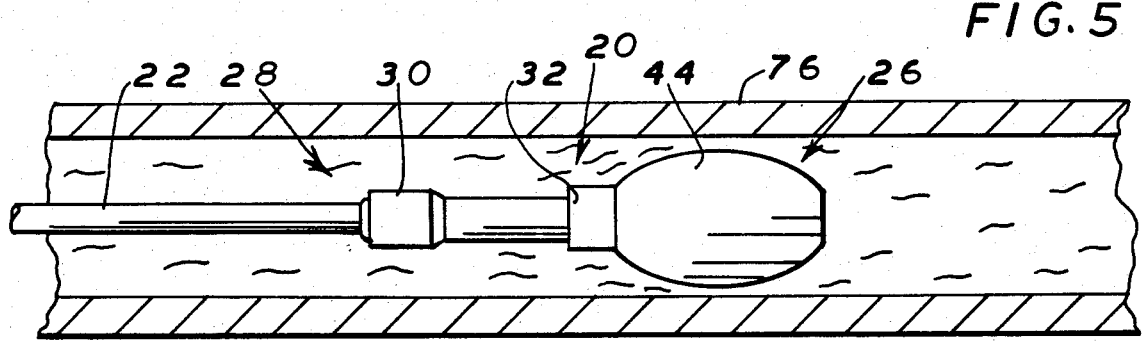
FIG. 5 is a fragmentary sectional view thereof showing the balloon in partial inflated form and being flow directed to the desired location in the vessel.
Figure 6:
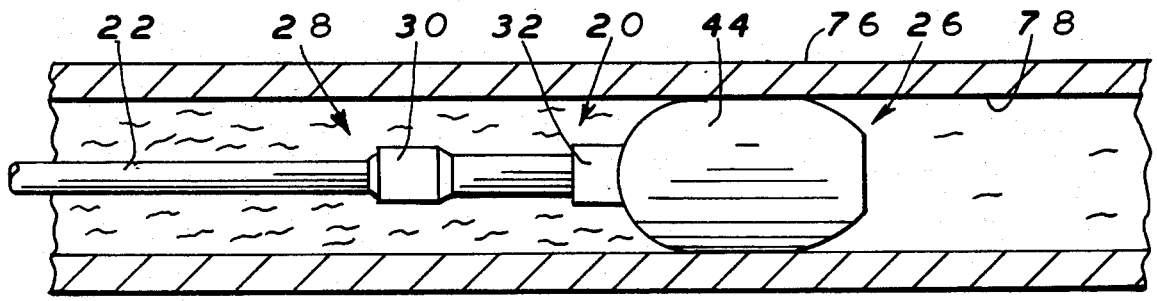
FIG. 6 shows the assembly in position with the balloon fully inflated to seal against the side walls of the vessel.

Turning to consideration of the sequence of operation as depicted in FIGS. 4 through 8 and the alternate use as depicted in FIG. 9, the catheter assembly 20 will be discussed and is depicted. FIG. 4 shows catheter assembly 20 in position in the small human vessel 76 prior to introduction of pressurized fluid to expand balloon 26. A first predetermined amount of pressurized fluid is then introduced as shown in FIG. 5 so as to partially expand balloon portion 44. This increases the lateral dimension of the catheter assembly 20 and gains the assistance of blood flowing through the vessel to push the assembly along through the vessel until it reaches the desired operable location. At that point, as shown in FIG. 6, further pressurized fluid is passed into the assembly so as to expand balloon portion 44 until it engages with the inner wall 78 of the vessel 76 and becomes fixed in position.

Thereafter, as shown in FIG. 7, a third stage of further pressurized fluid is passed through cannula 22. Since further expansion of balloon portion 44 is retarded by engagement with the walls of the vessel, the further fluid passes through side opening 48 in pin 36 and expands the proximal end portion 28 of balloon 26. The expansion of this portion which is between end 32 and cannula 22 frees it from engagement with cannula 22 and permits cannula 22 and pin 36 to be withdrawn from plug 34 and balloon 26. There is minimal resistance between bevel tip 46 and plug 34 due to the nature of the material of plug 34, and/or the preformed hole therein, and/or the type and degree of taper on tip 46. The cannula 22 and pin 36 can thus be removed from the assembly and from the vessel 76 leaving the inflatable balloon 26 in position as an implant as depicted in FIGS. 7 and 8.

Once pin 36 has been removed from plug 34 the self-sealing nature of plug 34 with the assistance of the resilience of the outer band 32, if necessary, causes the plug 34 to close the opening therethrough thereby forming a valve means to seal the inflated balloon portion 26 and retain it in an expanded position in proper location in the vessel 76.

Operation of the perfusion embodiment as depicted in FIG. 9, is accomplished in the following manner. Introduction of catheter assembly 20 is accomplished in the same manner as described above. The result brings assembly 20 into position in uninflated condition as shown in FIG. 4. A first amount of pressurized fluid is introduced to partially expand inflatable balloon portion 44 so that the blood flowing through the vessel assist in directing the assembly in the direction by engaging with the expanded balloon portion. When the assembly has reached the desired location along the length of the vessel 76, a further amount of pressurized fluid is passed through the assembly which fully expand balloon portion 44 into engagement with the inner wall 78 of the vessel. It fixes assembly 20 in position. Thereafter a third stage is reached at which additional fluid is introduced through cannula 32 from the fluid source. Balloon portion 44, as described above, is of a self-sealing inflatable material and in this embodiment is provided with a miniture hole or group of holes in the distal tip 80 as shown in FIG. 9. Therefore, since balloon portion 44 is retarded from further expansion due to its engagement with the wall 78 of the vessel, the further fluid forces the medicament or radiopaque dye contained within portion 44 out through the apertures in distal tip 80. Since portion 44 seals the vessel at the point of its location, the dye is not diluted by blood at the upstream end of the vessel and accordingly is fully effective in use at the point of perfusion.

As discussed above, the device can be a combination of the one depicted in FIGS. 1–8 and the one depicted in use in FIG. 9 so that perfusion can be produced and detachment achieved with perfusion continuing after the implant is made for a predetermined length of time. The amount of fluid introduced under pressure determines the necessary forces for perfusion and for detachment.

It is also possible to provide a cannula with a double lumen. One lumen would be connected to the pin that communicates to the balloon through the plug and the other lumen would communicate directly to the removal portion of the balloon.

Thus the several aforenoted objects and advantages are most effectively attained. Although several somewhat preferred embodiments have been disclosed and described in detail herein, it should be understood that this invention is in no sense limited thereby and its scope is to be determined by that of the appended claims.

We claim:

1. A miniaturized balloon catheter assembly adapted for use in diagnostic and therapeutic procedures in connection with small vessels comprising: a cannula having means at one end for attachment to a source of pressurized fluid and having a small outer diameter for insertion into small vessels, an inflatable tubular portion mounted on the other end of the cannula and in fluid communication therewith, the cannula and balloon portion adapted to be carried by the fluid in the vessel to a desired location therein, whereupon attachment of the cannula to a source of pressurized fluid and introduction of an amount of pressurized fluid flow inflate the balloon portion to fix it in position, and activation means responsive to a further amount of pressure to initiate a desired procedure within the small vessel at the desired location, said balloon portion being detachably connected to said cannula and having a sealing means thereon so that when the cannula and balloon portion are positioned in the desired location in the human vessel the cannula can be detached from the balloon portion whereupon the sealing means will seal the one end of the balloon portion, said sealing means including expandable, elastomeric self-sealing, plug material positioned in a mouth of the inflatable portion adjacent to the end of the cannula, a circumferential band on the outer surface of the inflatable portion in concentric position with respect to the plug material therein, a pin having a passageway therethrough and one end mounted in the end of the cannula with the passageway therein in communication with the passageway through the cannula and the other end of the pin extendable through a small opening in the plug material into fluid communication with the inflatable balloon portion on the side of the plug material distal from the cannula and when in that position expanding the surrounding band, a side opening intermediate the ends of the pin located in the space between the end of the cannula and the adjacent end of the plug material so that when sufficient pressurized fluid is passed through the cannula and pin into the inflatable portion to inflate the balloon to the desired amount, further fluid will pass through the side opening in the pin and inflate the end portion surrounding the plug material and extending to the end in communication with the cannula to thereby free the cannula and pin from the balloon portion for removal whereupon the band and self-sealing plug material will cooperate to close the opening in the plug material and retain the balloon in inflated condition.

2. The invention in accordance with claim 1 wherein the pin is an elongated cylindrical member with the end inserted in the plug material being circumferentially beveled to a point to facilitate penetration through the plug and removal of the pin from the plug material during detachment, the side opening in the pin being an arcuate cut-out in the side wall thereof to provide a lateral access to the through passageway in the pin, the end of the pin distal from the pointed end being of sufficient outer diameter to expand the cannula when inserted therein so as to provide a frictional interengagement therebetween and to provide a continuous passageway between the interior of the cannula and the interior of the pin for flow of fluid therethrough, and the frictional engagement between the end of the pin and the cannula being greater than the force of engagement between the pointed end of the pin and the plug material so that the cannula and pin can be removed from the plug material and balloon portion together upon a sufficient axial force applied to the cannula.

3. The invention in accordance with claim 1 wherein a wire extends through the cannula and pin into the balloon portion, the wire terminating in an enlarged stop so that removal of the wire toward the cannula will bring the stop into engagement with the tapered end of the pin and prevent further fluid from passing therethrough so that all further fluid introduced thereafter passes through the side opening in the pin thereby facilitating detachment of the pin and cannula from the balloon portion.

4. The invention in accordance with claim 1 wherein the pin is of substantially the same diameter for the portion thereof from the side opening to the end extending through the plug material with the edge extending through the plug material having a beveled edge, the portion of the pin from the side opening to the end thereof in communication with the cannula having a substantially larger outer diameter than the diameter of the pin including the side opening and the end extending through the plug material thereby facilitating attachment to the cannula by providing a larger outer diameter portion extending into the cannula to further expand the cannula and provide a tighter interengagement therebetween.

5. The invention in accordance with claim 1 with the cannula having a double lumen, one lumen is connected to the pin that communicates to the balloon portion through the plug material, the other lumen communicates directly to the removal portion of the balloon portion.

6. The invention in accordance with claim 1 wherein the circumferential band is formed of resilient material.

7. The invention in accordance with claim 1 wherein the other end of the pin is provided with a predetermined configuration to provide for minimal resistance between the pin and plug material to facilitate separation therebetween.

* * * * *